(12) United States Patent
Paul et al.

(10) Patent No.: US 11,262,425 B2
(45) Date of Patent: Mar. 1, 2022

(54) METHOD FOR ACQUIRING MAGNETIC RESONANCE DATA, MAGNETIC RESONANCE IMAGING APPARATUS, COMPUTER PROGRAM, AND ELECTRONICALLY READABLE STORAGE MEDIUM

(71) Applicant: Siemens Healthcare GmbH, Erlangen (DE)

(72) Inventors: Dominik Paul, Bubenreuth (DE); Flavio Carinci, Wuerenlingen (CH); Wilhelm Horger, Schwaig (DE); Mario Zeller, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 50 days.

(21) Appl. No.: 16/797,384

(22) Filed: Feb. 21, 2020

(65) Prior Publication Data
US 2020/0271741 A1 Aug. 27, 2020

(30) Foreign Application Priority Data
Feb. 25, 2019 (EP) .................................... 19159143

(51) Int. Cl.
*G01R 33/483* (2006.01)
*A61B 5/00* (2006.01)
(Continued)

(52) U.S. Cl.
CPC .......... *G01R 33/4835* (2013.01); *A61B 5/055* (2013.01); *A61B 5/7285* (2013.01);
(Continued)

(58) Field of Classification Search
CPC .............. G01R 33/4835; G01R 33/307; G01R 33/387; G01R 33/5616; G01R 33/5617; A61B 5/7285; A61B 5/055
See application file for complete search history.

(56) References Cited

U.S. PATENT DOCUMENTS 5,359,289 A * 10/1994 van der Meulen .... G01R 33/24
324/318
5,530,352 A 6/1996 Kolem
(Continued)

OTHER PUBLICATIONS

"Siemens medical", MR Glossary: https://www.depts.ttu.edu/research/ttni/downloads/MRGlossary.pdf (Year: 2008).*
(Continued)

*Primary Examiner* — Dixomara Vargas
(74) *Attorney, Agent, or Firm* — Schiff Hardin LLP (57) ABSTRACT

Techniques are disclosed for acquiring magnetic resonance data of an object with a magnetic resonance imaging apparatus. A slice group is imaged whose slices define a contiguous imaging volume and which contains a first number of slices. In a number of concatenations, the magnetic resonance data for subgroups of the slices, each containing a respective second number of slices depending on the first number of concatenations, are acquired, and shimming is performed to increase field homogeneity in the imaging volume. To define the subgroups, the imaging volume is subdivided into at least two disjoint contiguous sub-volumes, and at least two subgroups are defined for each sub-volume, each subgroup only containing non-adjacent slices in the sub-volume. During acquisition of the magnetic resonance data of each subgroup, shimming is at least restricted to the respective sub-volume.

14 Claims, 6 Drawing Sheets

(51) Int. Cl.
   G01R 33/30      (2006.01)
   G01R 33/387     (2006.01)
   G01R 33/561     (2006.01)
   A61B 5/055      (2006.01)

(52) U.S. Cl.
   CPC .......... *G01R 33/307* (2013.01); *G01R 33/387* (2013.01); *G01R 33/5616* (2013.01); *G01R 33/5617* (2013.01)

(56) References Cited

U.S. PATENT DOCUMENTS

| | | | | |
|---|---|---|---|---|
| 7,496,396 | B2* | 2/2009 | Harvey | G01R 33/54 |
| | | | | 324/307 |
| 10,429,464 | B2* | 10/2019 | Niederloehner | G01R 33/387 |
| 10,534,056 | B2* | 1/2020 | Deshpande | G01R 33/3628 |
| 2014/0002077 | A1* | 1/2014 | Deshpande | G01R 33/4835 |
| | | | | 324/309 |
| 2015/0260811 | A1* | 9/2015 | Blumhagen | G01R 33/3875 |
| | | | | 324/309 |
| 2017/0123027 | A1 | 5/2017 | Zuehlsdorff et al. | |
| 2018/0238979 | A1* | 8/2018 | Niederloehner | A61B 5/055 |
| 2019/0162807 | A1* | 5/2019 | Zahneisen | G01R 33/5611 |

OTHER PUBLICATIONS

Liu, Wei et al. "An Optimized Slice Acquisition Order in HASTE Imaging with a Short TR" Proceedings of the International Society for Magnetic Resonance in Medicine (ISMRM 2016), 24th Annual Meeting & Exhibition; Abstract No. 1808, Apr. 22, 2016.

European Search Report dated Sep. 5, 2019, for Application No. 19159143.7.

Bernstein, Matt A. et al. "Handbook of MRI Pulse Sequences" Chapter 11.5.2. Cross-Talk and Slice Ordering, Elsevier Academic Press, Amsterdam, pp. 410-415, 2004.

* cited by examiner

METHOD FOR ACQUIRING MAGNETIC RESONANCE DATA, MAGNETIC RESONANCE IMAGING APPARATUS, COMPUTER PROGRAM, AND ELECTRONICALLY READABLE STORAGE MEDIUM

CROSS-REFERENCE TO RELATED APPLICATIONS

The present application claims the benefit of the filing date of European patent application no. 19159143.7, filed on Feb. 25, 2019, the contents of which are incorporated herein by reference in their entirety.

TECHNICAL FIELD

The disclosure relates to a method for acquiring magnetic resonance data of an object, in particular a patient, with a magnetic resonance imaging apparatus.

BACKGROUND

Magnetic resonance imaging (MRI) is an established way to obtain diagnostic or other information in medical health care. To acquire magnetic resonance data of an imaging volume inside the patient, high frequency excitation pulses are used to excite the spins, which are aligned in a main magnetic field of the magnetic resonance apparatus. The decay of this excitation may be measured as the magnetic resonance signal. In recent years, this imaging process has been refined by many different imaging techniques. Most of these imaging techniques aim at achieving a better image quality, certain contrasts, and/or the reduction of scan time.

In particular, imaging techniques have been proposed which try to isolate protons bound in certain molecules, for example acquiring only magnetic resonance data regarding water while suppressing fat signals, or vice versa. These imaging techniques rely on the chemical shift between the Larmor frequencies of differently bound protons. For example, excitation pulses which are frequency selective may be used. In particular, regarding suppressing the signals of protons bound in fat, multiple fat saturation techniques have been proposed such as chemical shift selective saturation, water excitation, and spectral attenuated inversion recovery (SPAIR). However, these fat saturation techniques are sensitive to local Larmor frequency offsets, which may result from an inhomogeneous spatial distribution of the static main magnetic field. Such inhomogeneities may, in particular, also occur due to the object to be imaged. In regions in which such field inhomogeneities occur, the fat saturation may be compromised. This is mainly due to the fact that fat saturation techniques require the use of frequency selective pulses which act on the whole imaging volume, where strong field inhomogeneity in the order of the mentioned chemical shift can occur, especially at higher magnetic field strength.

SUMMARY

An established tool to counteract inhomogeneities of the main magnetic field is called shimming. In dynamic shimming, shim coils are controlled to produce magnetic shim fields which, at least in part, compensate inhomogeneities in a certain shim volume, which may also be called the "shim box." Field inhomogeneities at least inside such a shim box may be measured, for example using known main magnetic field (BO) mapping methods, where after shim currents in the shim coils may be calculated such that the resulting magnetic shim fields at least partly compensate the measured inhomogeneities. It has been proposed to vary such shim settings for each slice to be acquired by choosing the slice volume or at least a region of interest inside the slice volume as the shim box. These shimming approaches focusing on improving the homogeneity only in a certain localized shim box are also known as "local dynamic shimming" or simply "local shimming" In this context, local shimming works best if a localized shim box may be used which has a very small geometric extension. In other words, it is easier to compensate inhomogeneities in smaller volumes than in larger volumes.

Known approaches thus use local shimming, in particular in combination with frequency adjustments, focused on a region of interest, which is also used as the shim box. With this approach, the static field homogeneity in the region of interest is improved by a particular setting for the currents of the shim coil and by selecting an optimal resonance frequency for the given conditions.

In imaging volumes, defined by a slice stack (slice group) of a first number of slices, which are subject to motion, in particular breathing motion, of a patient, it has been proposed to acquire all slices in the same general motion state, that is, the motion states during acquisition of all slices should at least essentially match. Regarding periodic motions like breathing, intervals can be defined, during which the motion state does not change in a relevant way. Imaging can then be limited to these time intervals, pausing in between, by, for example, using triggering at the beginning of these intervals. As a trigger signal, navigator data and/or sensor data regarding the periodic motion may be used.

However, usually not all of the slices of the slice group can be acquired during the duration of these intervals. Thus, it has been proposed to use multiple so-called concatenations (concats), wherein, in each concatenation, a second number of slices in a certain subgroup are imaged consecutively during the duration of the interval. To reduce possible slice crosstalk effects, it has been proposed to maximize the geometric distance between the slices to be acquired for all concatenations. For example, if 30 slices are to be acquired in 6 concatenations, the first subgroup will be chosen as comprising slices 1, 6, 11, 16, 21, 26, the second concatenation will use a subgroup consisting of slices 2, 7, 12, 17, 22 and 27, and so on.

In combination with local shimming techniques, homogeneity has to be improved for all slices to be acquired in one concatenation, that is, usually the whole imaging volume is defined as the shim box. However, when imaging larger regions of interest, for example the abdomen, thorax, or pelvis, the limits of the spatial effectiveness of local shimming may be exceeded. This may lead to local shimming not being applicable such that the image quality, in particular regarding fat saturation techniques, may not be improved.

Thus, to address these issues the present disclosure relates to a method for acquiring magnetic resonance data of an object, in particular a patient, with a magnetic resonance imaging apparatus, wherein a slice group, whose slices define a contiguous imaging volume and which contains a first number of slices, is imaged, wherein in a first number of concatenations the magnetic resonance data for subgroups of the slices, each containing a respective second number of slices depending on the first number of concatenations, are acquired, and wherein shimming is performed to increase field homogeneity in the imaging volume. The disclosure further concerns a magnetic resonance imaging apparatus, a computer program, and an electronically readable storage medium.

It is an object of the current disclosure to improve the performance of local shimming for multiple concatenation imaging, in particular when using fat saturation techniques in triggered image acquisition scenarios.

This object is achieved by providing a method as discussed herein and according to the independent claim 1, a magnetic resonance imaging apparatus as discussed herein and according to independent claim 13, a computer program as discussed herein, and an electronically readable storage medium as discussed herein and according to independent claim 15. Advantageous embodiments are further described throughout the disclosure as well as in the dependent claims.

In a method as initially described, to define the subgroups, the imaging volume is subdivided into at least two disjointed (e.g. disconnected or separate) contiguous sub-volumes, and at least two subgroups are defined for each sub-volume, each subgroup only containing non-adjacent slices in the sub-volume, wherein, during acquisition of the magnetic resonance data of each subgroup, shimming is at least restricted to the respective sub-volume.

The disclosure thus proposes the use of a specific slice reordering and splitting algorithm, which allows to reduce the shim box from the size of the imaging volume to the size of the respective sub-volume associated with a subgroup to be imaged in one concatenation or even, preferably, the smallest bounding box of the actually acquired slices of the subgroup. That is, the shimming may be restricted to the smallest possible bounding box of the slices in the subgroup during each concatenation. In this embodiment, the shim box for which shim settings of the local shimming technique, e.g. shim currents of respective shim coils of a shimming device, are determined may be chosen even smaller than the sub-volume, namely as the smallest possible volume still containing all slices of the subgroup. It is noted in this context that, usually the embodiments of the present disclosure will be applied in cases in which the acquisition of each concatenation is spaced in time from the acquisition of the other concatenations, for example until a certain motion state or interval reoccurs when triggering regarding periodic motion. Generally, splitting up the slices of the full slice group in a way to reduce the size of the shim box for local shimming allows improvement of the local shimming, and thus the image quality.

It should be noted that the shim settings are, of course, updated for each concatenation or at least each updated shim box. That is, dynamic adjustments are effected by using the optimal shim box for each concatenation, such that a better image quality thanks to a more homogeneous static magnetic field inside the imaging volume is provided. If, in an embodiment, for acquisition of the magnetic resonance data, at least one frequency selective preparation pulse is used as a high-frequency excitation pulse, the preparation is also improved due to the increased homogeneity in the area covered by the slices by the current subgroup. As an example, a fat saturation technique using the preparation pulses as discussed herein may be implemented.

Generally, in the method according to the disclosure, the first number of concatenations to be used is usually determined depending on the maximum second number of slices to be allowed in one subgroup, considering a distribution of slices to the subgroups as even as possible. For example, if a triggered acquisition, e.g. in a free breathing scenario, is used, as will be further explained below, there may be a maximum number of slices which can be acquired in one interval of a certain duration, for example defined by an essentially similar motion state throughout or as a certain movement phase. This maximum is also the maximum number of slices that can be acquired during one concatenation. In such a case, the total, that is first, number of concatenations is preferably adapted.

The slices are, in consequence, distributed as evenly as possible to the subgroups. For example, the second number of slices will be the integer quotient resulting from Euclidian division of the first number of slices by the first number of concatenations or the integer quotient plus one, wherein the latter case only occurs when the modulus is not zero. If the modulus is zero, the first number of concatenations multiplied by the second number of slices equals the first number of slices. Usually, in the case of a modulus being non-zero, different second numbers of slices may be acquired in different concatenations. Alternatively, at least one subgroup of at least one concatenation may comprise "leftover" slices, or even be filled up with "dummy" slices and/or reacquisitions of already imaged slices.

In a next step, sub-volumes of the imaging volume are defined, with each sub-volume containing a certain third number of slices, which may, as discussed below, differ for different sub-volumes. The third number of slices is any sum of allowed second numbers of slices, as explained above. For example, the imaging volume is subdivided along the slice direction, that is, the direction along which the slices are stacked. For each of these sub-volumes, subgroups containing the second number of slices are defined such that all slices lie inside the current sub-volume. In this manner, at least two subgroups, and thus two concatenations, are defined for each sub-volume such that no directly-adjacent slices are consecutively imaged to prevent slice crosstalk. As soon as the concatenations are performed (i.e. all slices of each subgroup are imaged consecutively) local shimming may be restricted using a shim box which may be the respective sub-volume, but which may be preferably the smallest possible bounding box of the slices in the subgroup.

As a consequence of the embodiments as described herein, each sub-volume is associated with a second number of concatenations, such that by imaging the slices of each subgroup of these concatenations, the whole sub-volume is imaged. In some embodiments, the second number of concatenations (i.e. the number of subgroups whose slices define the extent of the respective sub-volume), is chosen from the group comprising two and three.

It is noted that to perform the methods as described above and elsewhere herein, a person skilled in the art will conclude that the first number of slices may be larger than seven, and the first number of concatenations may be larger than three (e.g., larger than five). For example, if the slice group comprises eight slices, two sub-volumes each comprising four slices may be defined such that four concatenations with subgroups of two slices each may be defined such that the two slices of each subgroup are non-adjacent in each sub-volume.

In the following, illustrative examples for certain properties of the number of concatenations are provided, which each form advantageous concrete embodiments of the present disclosure.

As an example, if the volume of concatenations is even, each sub-volume is defined to be associated with a second number of concatenations equal to an even divisor of the number of concatenations. As already mentioned, the second number of concatenations may be for example two and/or three, in this example two. Continuing this example, two concatenations may be associated with each sub-volume such that the number of sub-volumes is half the number of concatenations.

In accordance with the current example, the concatenations may thus be grouped in pairs. If, for example, thirty slices are in the slice group and six concatenations are planned, each concatenation will acquire magnetic resonance data from five slices. For example, the first pair of concatenations may then cover the first ten slices (that is, the sub-volume defined by slices one to ten), the next pair may cover the next ten slices, and so on. For the first pair of concatenations, slices 1, 3, 5, 7 and 9 may be acquired, while the second concatenation of the first pair may be used to acquire the slices 2, 4, 6, 8 and 10. With this approach, the slices of the concatenations are geometrically close together such that, as described, a localized shim box can be used to cover only slices in these concatenations. In addition, there are no two slices that are directly adjacent and to be acquired in the same concatenation.

In accordance with the present embodiment, or as an additional or alternative embodiment, if the first number of concatenations is uneven, an uneven number of sub-volumes is defined to be associated with an uneven second number of concatenations. That is, to associate second numbers of concatenations with each sub-volume, if an uneven first number of concatenations is given to at least one sub-volume, an uneven second number of concatenations (e.g. three) has to be assigned.

In an illustrative example, if the number of concatenations is five, this approach leads to a single possibility, namely having a first sub-volume whose slices are acquired in two concatenations and a second sub-volume whose slices are acquired in three concatenations. However, this case is suboptimal and should, when possible, be avoided. In the case of five total concatenations, the pairing discussed regarding the even first number of concatenations can only be done at one end of the slice stack, while the other end has to use three concatenations for that particular sub-volume. This second sub-volume is more than half the size of the imaging volume, such that there may be a smaller shim box definable. The advantage is, however, less than when at least three sub-volumes are definable.

It is noted that the case of four concatenations is, for the same reasons, also not preferred. Options to avoid those unwanted first numbers of concatenations are discussed below.

If the number of concatenations is larger than five and uneven, one sub-volume associated with three concatenations and several sub-volumes associated with two concatenations may be defined. Preferably, the sub-volume associated with three concatenations is placed central along the stack of slices, such that the other sub-volumes surround the one sub-volume. In such an embodiment, outer concatenations may be paired as described above with reference to an even first number of concatenations. The residual inner slices will be split up to be imaged in three concatenations. In an example with twenty-eight slices in the slice group and seven concatenations, the first eight slices of the slice stack form a first sub-volume, the middle twelve slices of the slice stack form a second sub-volume and the last eight slices of the slice stack form a third sub-volume. The first sub-volume is imaged in two concatenations, the second sub-volume in three concatenations and the third sub-volume in two concatenations.

In a special case, namely, if the first number of concatenations is divisible by the uneven second number of concatenations, all sub-volumes are defined that such they are associated with the uneven second number of concatenations. For example, in the case of nine or twelve concatenations, instead of pairing two concatenations, as described above, three concatenations may be assigned to each sub-volume, this time using three sub-volumes in the case of nine concatenations or four sub-volumes in the case of twelve concatenations.

In an embodiment, it is also conceivable, that, during acquisition, concatenations associated with subgroups of slices in different sub-volumes may be imaged adjacent in time such that slice crosstalk may be further reduced.

As already described above, it is possible to handle unfavorable numbers of concatenations by addition or redistribution of slices. In an embodiment, at least one admissibility criterion describing first numbers of concatenations to be avoided is evaluated, wherein, if a first number of concatenations to be avoided is detected by the admissibility criterion, additional slices and/or additional acquisitions of slices already in the slice group are added as at least one additional concatenation, and the first number of concatenations is accordingly increased. The admissibility criterion may check whether the first number of concatenations is smaller than a predetermined value (e.g. six). In this manner, it can be assured that at least three sub-volumes are definable, substantially reducing the size of shim boxes.

It is noted, however, that slices or acquisitions should only be added as long as there are no relevant restrictions imposed by the measurement parameters, for example regarding the SAR limit and/or the repetition time TR.

In an embodiment, magnetic resonance data from the additional slices and/or acquisitions may be used as a navigator and/or to equalize concatenation distribution in a continuous measurement involving multiple different positions of a patient table of the magnetic resonance apparatus. Additional slices could either be included into the final reconstructed slice stack data/magnetic resonance image presented to the user, or may be discarded in a later step. If the magnetic resonance data of the additional slices is to be discarded, the acquisition can be performed as a dummy scan. However, arbitrary phase encoding can be employed, for example, to obtain additional navigator data.

To provide an example in which slice groups are to be acquired at multiple different positions of a patient table of the magnetic resonance apparatus, the problem of an undesired first number of concatenations can also be solved by redistributing slices between these multiple stations to achieve an optimal distribution of concatenations for all these positions of the patient table.

In embodiments, the acquisition of each subgroup, that is, each concatenation, may be triggered using a trigger signal describing a phase of a periodic motion of a patient to be imaged, and/or the first number of concatenations may be determined automatically depending on a measurement of the periodic motion of the patient. The trigger signal may describe, for example, a breathing cycle phase, which is, in many cases, the most relevant motion encountered. However, the trigger signal may also additionally or alternatively describe a heart cycle phase of the patient. Such trigger signals may, for example, be determined using a dedicated sensor and/or navigator measurements ("Pilot Tone" technique) and/or may describe the beginning of an interval suitable for acquisition. Prospective Acquisition Correction (PACE) may also be performed, which comprises a learning phase from which breathing characteristics may be extracted.

While the first number of concatenations may be preset (i.e. predetermined), it has also been proposed to automatically adapt the first number of concatenations to the breathing characteristics of the current patient. This adaptation may be performed, for example, during the learning phase of PACE triggering and/or based on the breathing statistics when using a respiratory sensor and/or navigator measurements.

In an embodiment, a Turbo Spin Echo sequence (TSE) may be used for acquiring the magnetic resonance data. However, the implementations of the embodiments as described herein are not limited to the use of TSE sequences, but are also advantageous when implemented using single- and multi-shot Echo Planar Imaging (EPI) sequences, where, for example, insufficient fat saturation may lead to fat ghosting in the anatomy.

The disclosure also concerns a magnetic resonance imaging apparatus, comprising a control device having a controller and a memory, wherein the control device is configured to perform the steps of a method according to the disclosure as discussed herein. All features and remarks regarding the method according to the disclosure also apply to the magnetic resonance imaging apparatus according to the disclosure.

For example, functional units may be implemented by the control device, such as the controller. These functional units may be implemented using software and/or hardware. For example, the control device may comprise, as already known in the state of the art, an acquisition unit controlling the acquisition of magnetic resonance data. Additionally, a subdividing unit for defining the sub-volumes, an allocation unit for assigning the slices of each sub-volume to subgroups to be imaged in respective concatenations, and a shimming unit for controlling a shimming device of the magnetic resonance imaging apparatus, for example using the downsized shim boxes described above.

A computer program according to the disclosure can be loaded directly into a memory of a control device of a magnetic resonance imaging apparatus, and comprises program means to perform the steps of a method according to the disclosure if the computer program is executed in the control device of the magnetic resonance imaging apparatus. The computer program may be stored on an electronically readable storage medium, which thus comprises electronically readable control information stored thereon, which comprises at least one computer program according to the disclosure and is configured to perform the steps of a method according to the disclosure if the storage medium is used in a control device of a magnetic resonance imaging apparatus. The electronically readable storage medium according to the disclosure may be a non-transitory computer-readable medium storage medium, for example a CD-ROM. Thus, the functions associated with the method embodiments and/or other embodiments as described herein may be implemented, for example, via the execution of the instructions (e.g. program code) stored on the storage medium, which may be executed by one or more suitable processors (e.g. processors associated with the control device of the magnetic resonance imaging apparatus and/or other suitable components associated with the magnetic resonance imaging apparatus).

BRIEF DESCRIPTION OF THE DRAWINGS/FIGURES

Further details and advantages regarding the current disclosure may be taken from the following description of example embodiments taken in conjunction with the drawings, in which.

DETAILED DESCRIPTION

Figure 1:
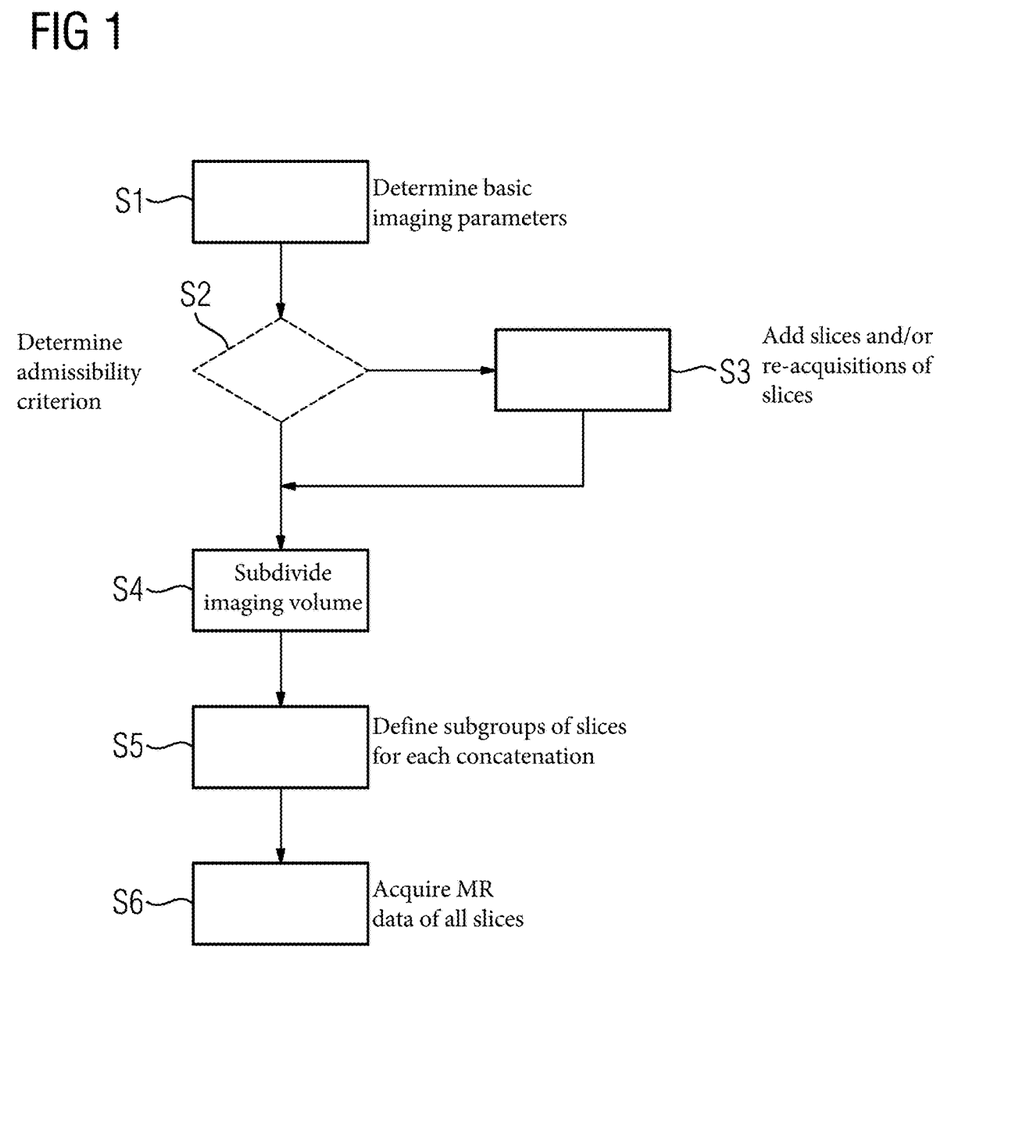
FIG. 1 is a flow chart of an example method, in accordance with an embodiment of the present disclosure.

FIG. 1 is a flow chart of an example method, in accordance with an embodiment of the present disclosure. The method serves to acquire magnetic resonance data from an imaging volume inside a patient, wherein, in this example, a large imaging volume is used, for example the thorax, the pelvis, or the abdomen. The imaging volume is subject to the breathing motion of the patient. However, the acquisition of magnetic resonance data described here is to be done at free breathing, such that slices will be acquired at a certain phase of the breathing cycle. This breathing phase defines a certain interval during which, however, not all the slices may be acquired such that multiple concatenations are used.

In a step S1, basic imaging parameters are determined. First, automatically or specified by a user, the first (total) number of slices to be acquired and their positioning is determined. That is, the imaging volume is defined by a slice stack built from a first number of slices, which are all in a slice group. For example, thirty slices may form the slice group and define the imaging volume.

Since the breathing characteristics of the patient also influences the number of slices that may be acquired during each breathing cycle without too much motion occurring, these breathing characteristics are determined and used to check if the total number of concatenations (first number of concatenations) to be used is to be adapted, starting from a predetermined value of, for example, five or six.

In embodiments, the trigger signal describing the breathing motion of the patient may be acquired using, for example, a dedicated sensor and/or navigator data acquired in a navigator scan using the magnetic resonance imaging apparatus. Navigator sequences to acquire navigator data are known in the state of the art and may, for example, be one-dimensional sequences measuring the position of an edge of the diaphragm. If PACE is used, a measurement of the breathing motion of the patient may be performed during a learning phase. In any case, breathing characteristics may be determined depending on which the number of concatenations are to be actually used, and thus the maximum second number of slices to be consecutively acquired in one of these concatenations can be determined. For example, the second number of slices to be imaged during one concatenation may either be an integer divisor of the first number of slices in the slice group and the first number of concatenations or the divisor plus one, as long as the modulus is not zero. If the modulus is zero, all concatenations will consecutively acquire the same second number of slices, namely the integer divisor.

In the present example, a fat saturation technique is used, which may be a SPAIR technique or a classical so-called FatSat technique. Both of those techniques use frequency selective high-frequency preparation pulses as excitation pulses. The effectiveness of these preparation pulses highly depends on the homogeneity of the static main magnetic field of the magnetic resonance imaging apparatus. Thus, local shimming is to be used to improve the homogeneity of the static main magnetic field in the imaging volume.

However, as initially explained, in this case, a very large imaging volume is used such that local shimming of the whole imaging volume as the shim box may not be possible or at least not to the desired grade. Thus, in the method described here, a reordering and allocation of slices to certain sub-volumes of the imaging volume is performed, such that only slice groups in a single sub-volume are imaged in each concatenation, and the shim box can be respectively minimized.

First, however, in an optional step S2, an admissibility criterion may be evaluated. The admissibility criterion checks if an undesired first number of concatenations has been determined in step S1. For example, it can be checked whether the first number of concatenations is lower than six, since, in that case, only two sub-volumes could be defined such that the shim box may be only approximately half the size of the imaging volume. In the case that the admissibility criterion is fulfilled, in a step S3, additional slices and/or reacquisitions of slices may be added to increase the first number of concatenations. While, if the magnetic resonance data of these additional slices or reacquisitions is to be discarded, these scans may later be performed as dummy scans, and it is preferable to use these additional acquisitions to generate more navigator data, such as by using arbitrary phase encoding, for instance.

In any case, in a step S4, the imaging volume is subdivided into sub-volumes, in this embodiment such that the slices of each sub-volume may be imaged with two or more concatenations. For example, if required, a maximum of three concatenations may be set, although any suitable number of concatenations may be used depending upon the particular application.

Thus, if the first number of concatenations is even, in step S4, the imaging volume is subdivided such that magnetic resonance data for each sub-volume may be acquired in two concatenations. It is, however, also possible, if the even number is divisible by three, to define sub-volumes which may be acquired with three concatenations. It may be preferred, however, to pair the concatenations to have sub-volumes geometrically as small as possible.

If the first number of concatenations is uneven, at least one sub-volume may be imaged using three concatenations. If possible, the sub-volume to be imaged in three concatenations is positioned in the middle of the imaging volume, such that at least one sub-volume that can be imaged in two concatenations follows on each side in the stacking direction of the slices. In the case of the first number of concatenations being divisible by three, again, for example in the case of nine total concatenations, all sub-volumes may also be defined to be imaged in three concatenations.

In a step S5, subgroups of slices for each concatenation are defined, that is, the slices of the sub-volumes are allocated to concatenations which are restricted to these sub-volumes, such that no directly adjacent slices are imaged in the same concatenation to prevent slice crosstalk.

The result of steps S4 and S5 is, in the following, illustrated for multiple examples of first numbers of concatenations as shown and further discussed below with respect to FIGS. 2 to 5.

In step S6, the magnetic resonance data of all slices of the slice group are acquired, wherein dynamic local shimming is applied. In the current embodiment, the shim box describing the region in which the static main magnetic field during each concatenation should be homogenized is chosen as the smallest bounding box of the slices to be acquired in one concatenation, which will often be even smaller than the corresponding sub-volume. In this way, a geometrically small shim box is established, improving the quality of the local shimming and thus the quality of the fat saturation.

Figure 2:
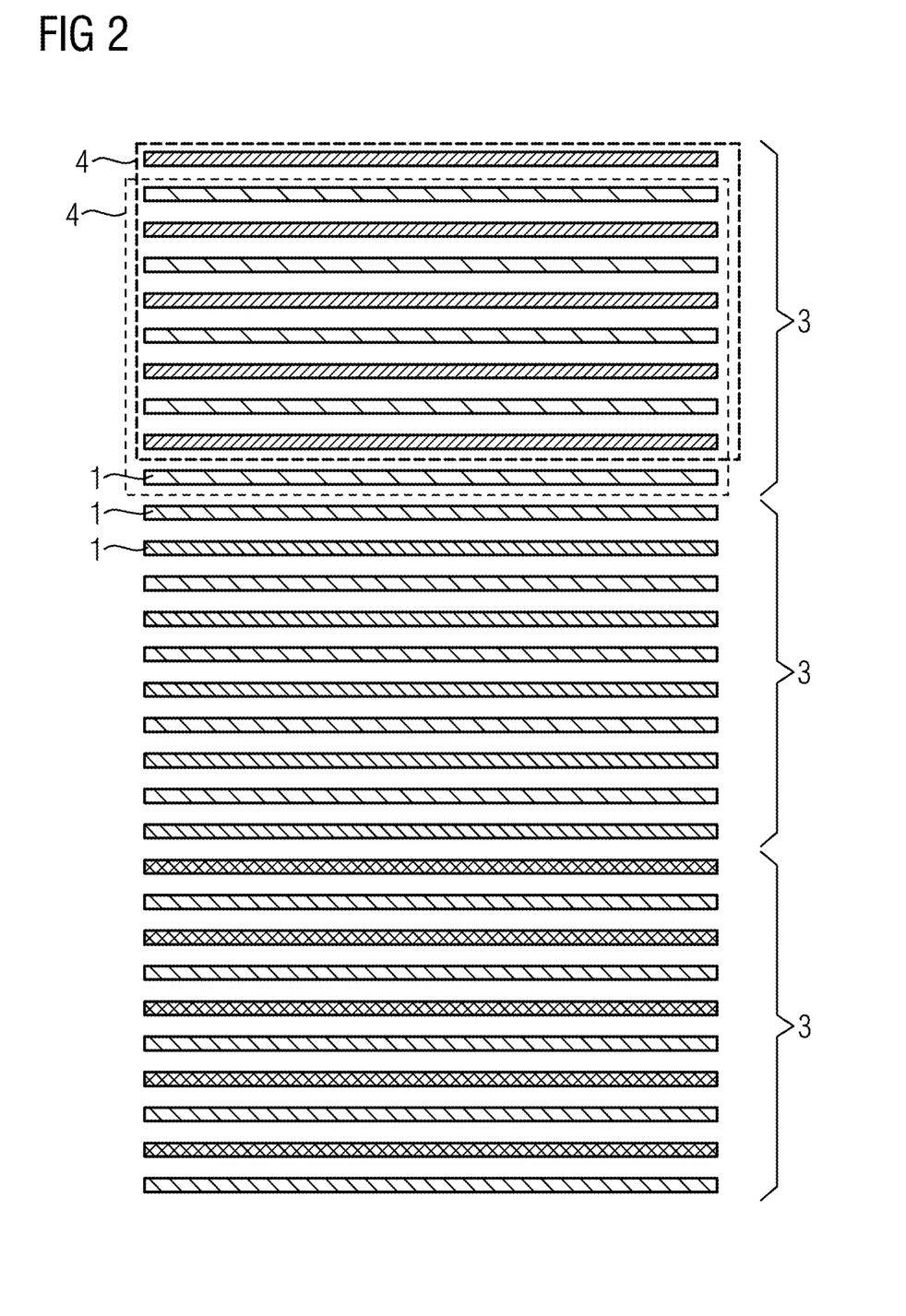
FIG. 2 shows an example allocation of slices to different sub-volumes and subgroups in a first case, in accordance with an embodiment of the present disclosure.

In FIG. 2, an example for a slice group having thirty slices 1 is illustrated. In this case, as thirty is divisible by six, yielding five, the second number of slices to be acquired is five for each concatenation. The imaging volume 2 defined by the entirety of the slices 1 is subdivided into three sub-volumes 3, each comprising ten slices 1. Each of these sub-volumes 3 can thus be imaged in two concatenations. In a first concatenation for the first sub-volume 3, the first, third, fifth, seventh, and ninth slices 1 are acquired. In a second concatenation for the first sub-volume 3, the second, fourth, sixth, eighth, and tenth slices 1 are acquired. Slices imaged in different concatenations are depicted differently in FIG. 2.

FIG. 2 also shows the smallest possible bounding box 4 for the first two concatenations associated with the first sub-volume 3, which are to be used as shim boxes for the dynamic local shimming.

Figure 3:
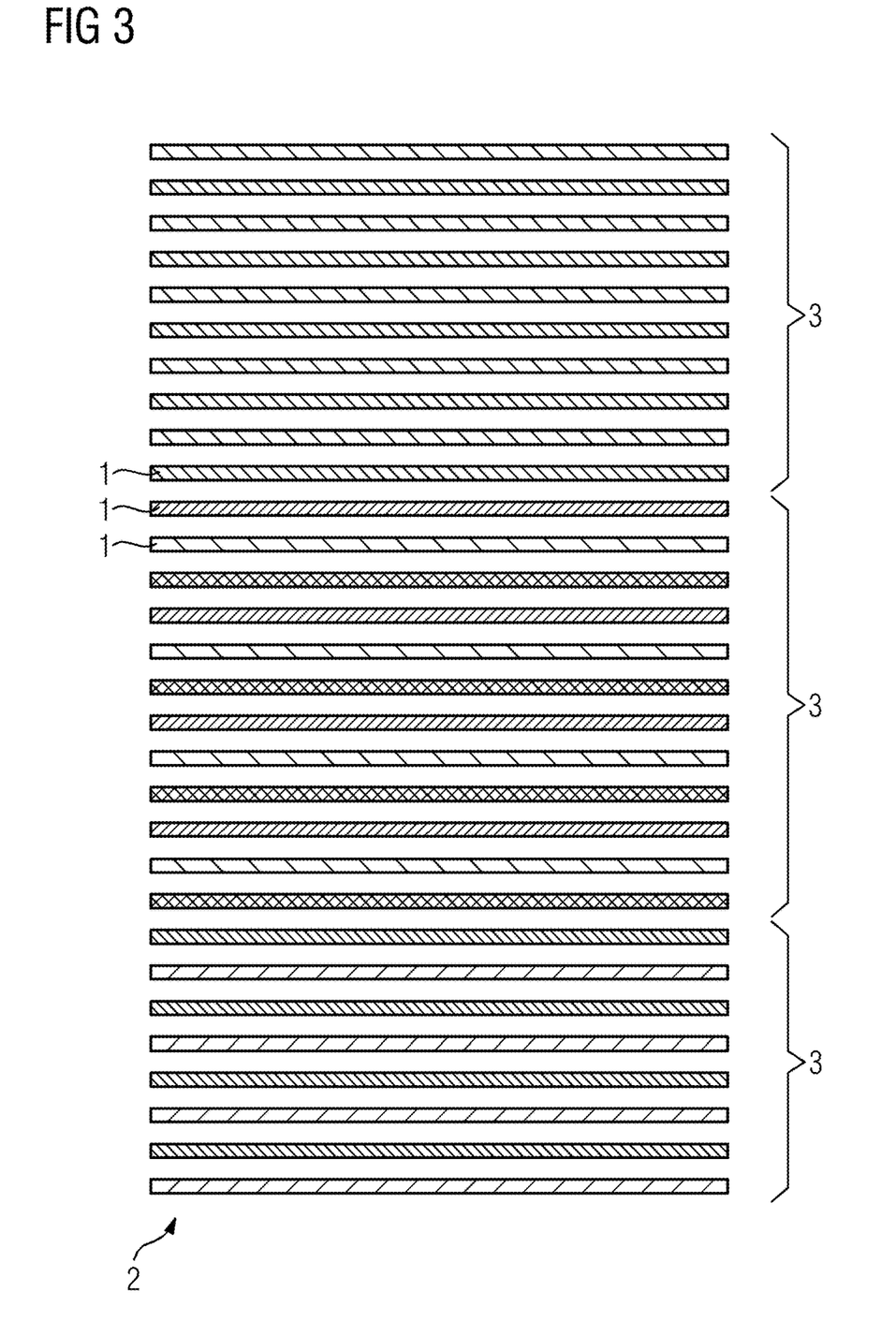
FIG. 3 shows an example allocation of slices to different sub-volumes and subgroups in a second case, in accordance with an embodiment of the present disclosure.

FIG. 3 shows a second example in which the thirty slices 1 are to be imaged in seven concatenations. In this case, two concatenations image five slices, the other five concatenations image four slices each. Additionally, since seven is an uneven first number of concatenations, one sub-volume 3 is defined, which is to be imaged in three concatenations.

Thus, as can be seen from FIG. 3, three sub-volumes 3 have been defined, the first sub-volume 3 containing ten slices 1 to be imaged in the first two concatenations, whose slice groups contain five slices each, the second sub-volume containing twelve slices 1, which are to be imaged in three concatenations, and the third sub-volume 3 containing eight slices 1 to be imaged in two concatenations. As in FIG. 1, the allocation of the slices 2, the slice groups, and thus concatenations, is indicated by a different depiction for each sub-volume 3.

As can also be seen, on both sides of the central, three-concatenation sub-volume 3, one two-concatenation sub-volume 3 adjoins.

Figure 4:
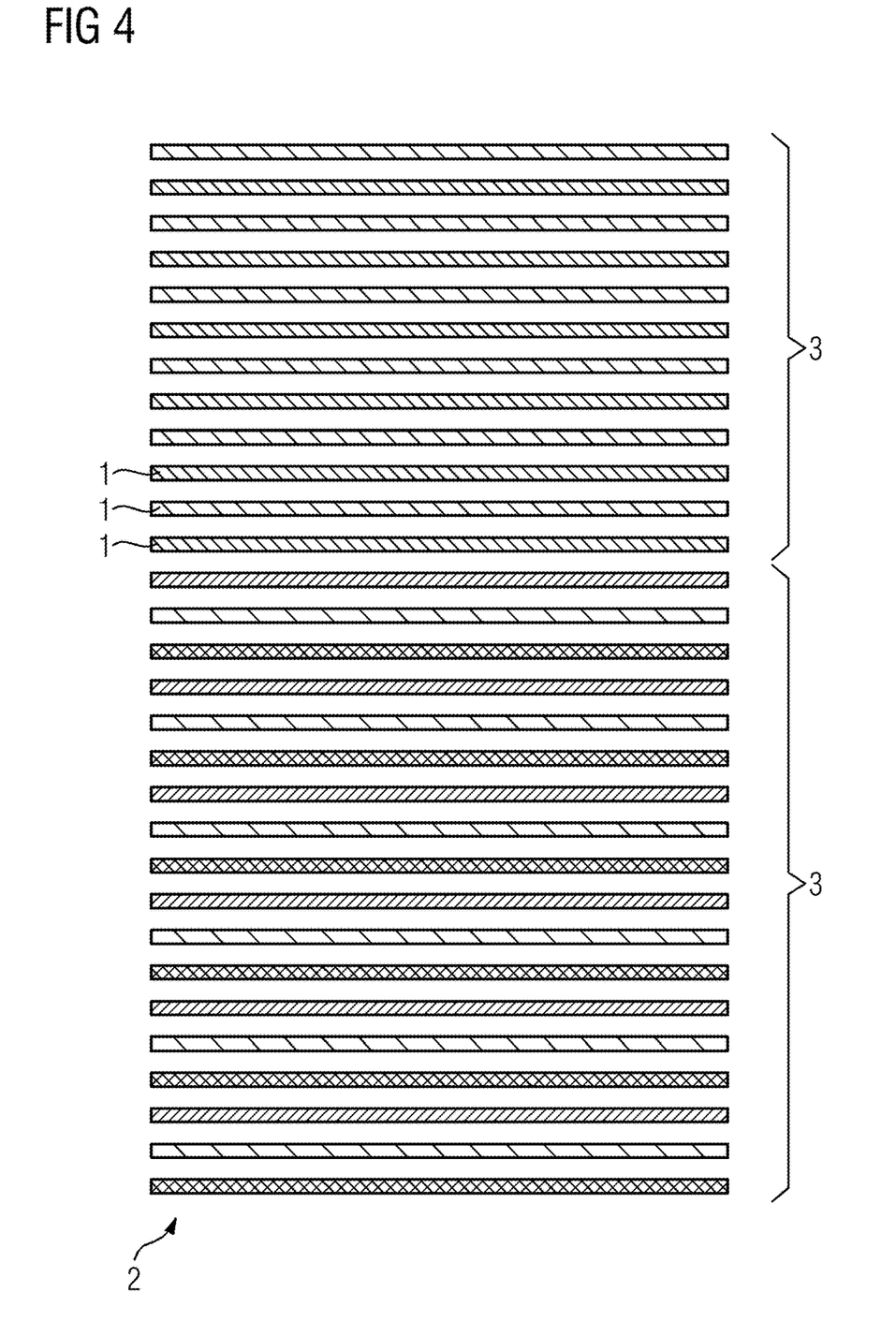
FIG. 4 shows an example allocation of slices to different sub-volumes and subgroups in a third case, in accordance with an embodiment of the present disclosure.

In FIG. 4, an example for five concatenations is shown, such that in each concatenation, a subgroup comprising six slices is to be acquired. However, in this case, only two sub-volumes 3 are defined: one sub-volume 3 containing twelve slices to be imaged in two concatenations, and one sub-volume 3 containing eighteen slices to be acquired in three concatenations. However, in such a case, it may be advantageous to add additional slices or reacquisitions of slices, as discussed regarding step S2, to end up with six concatenations enabling the definition of three sub-volumes, as shown in FIG. 2.

Figure 5:
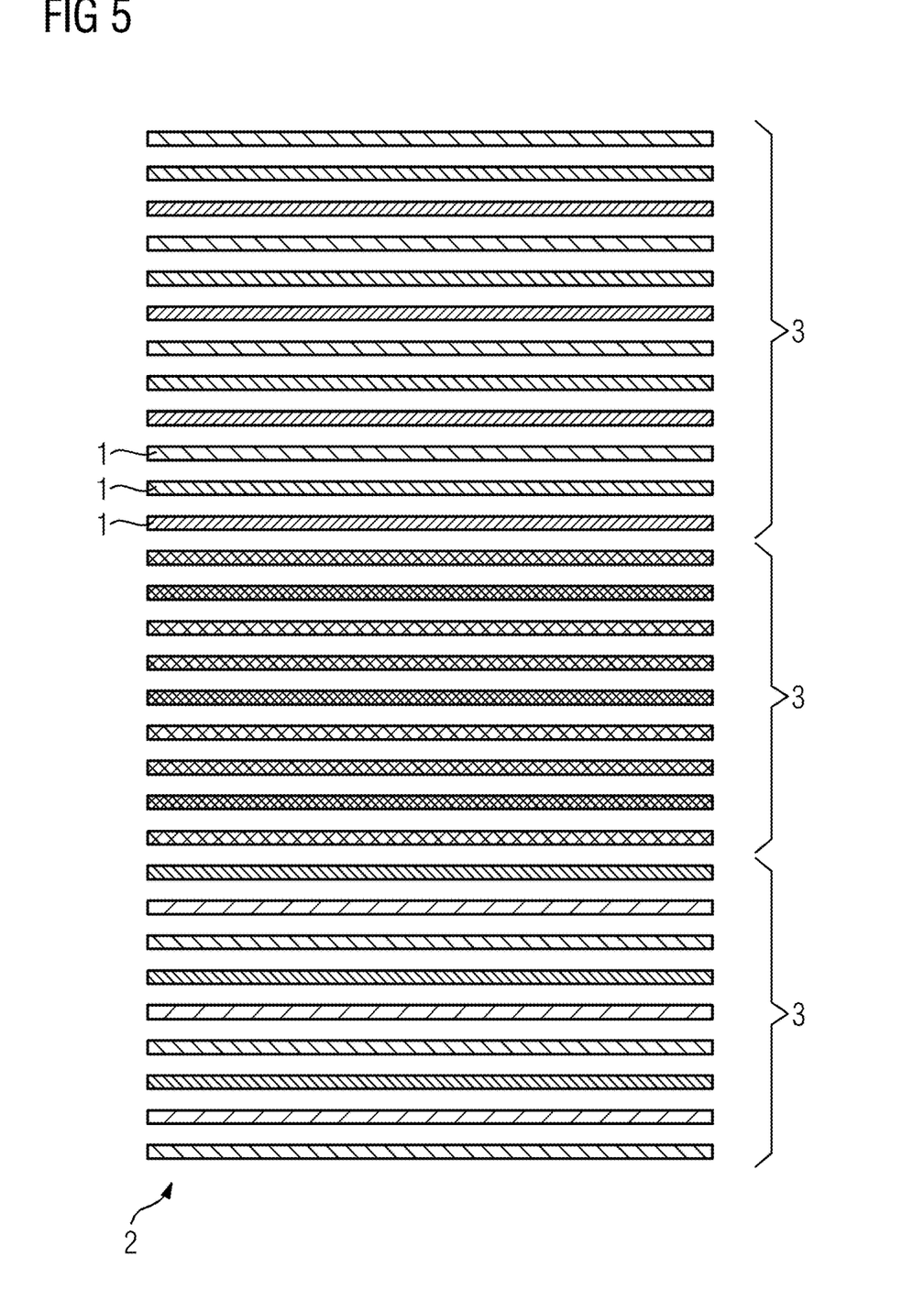
FIG. 5 shows an example allocation of slices to different sub-volumes and subgroups in a fourth case, in accordance with an embodiment of the present disclosure.

FIG. 5 finally shows an example for nine total concatenations. In this case, three sub-volumes 3 have been defined, such that the first sub-volume 3 has twelve slices, and the second and third sub-volumes 3 each have nine slices. That means that all sub-volumes may be imaged using three concatenations, wherein the concatenations in the first sub-volume 3 acquire four slices each, the other concatenations acquire three slices each.

Figure 6:
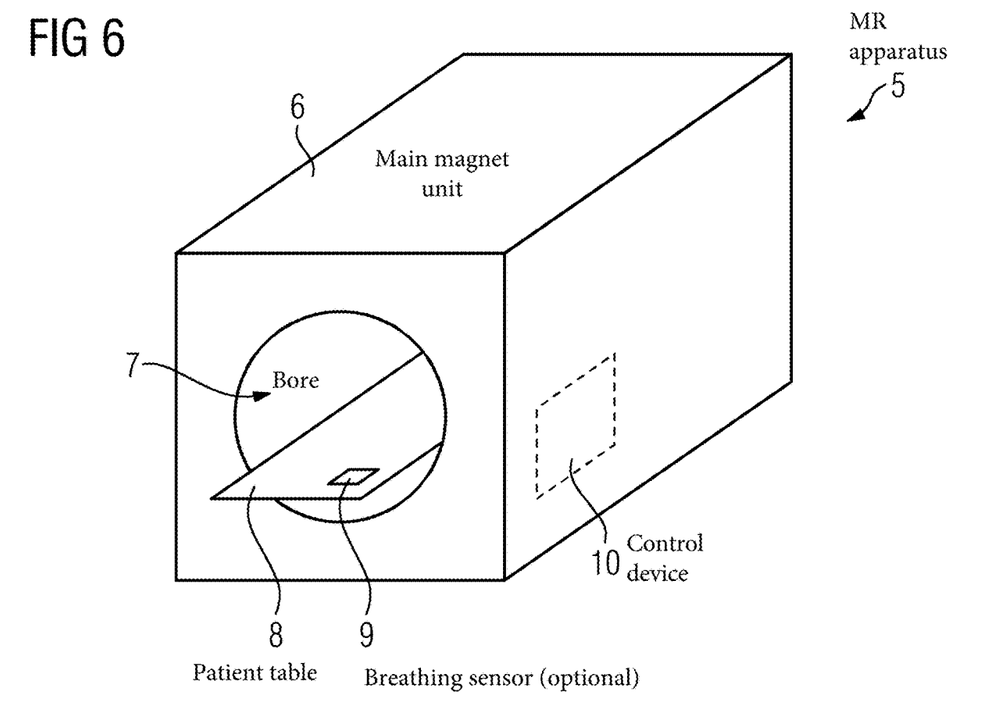
FIG. 6 illustrates an example magnetic resonance imaging, in accordance with an embodiment of the present disclosure.

FIG. 6 shows a principle drawing of a magnetic resonance imaging apparatus 5 according to the disclosure. As shown, the magnetic resonance imaging apparatus 5 comprises a main magnet unit 6 defining a bore 7 in which a patient may be positioned using the patient table 8. Indicated on the patient table 8 is an optional breathing sensor 9.

The magnetic resonance imaging apparatus 5 is controlled by a control device 10. The control device 10 is configured to perform a method according to the disclosure.

Figure 7:
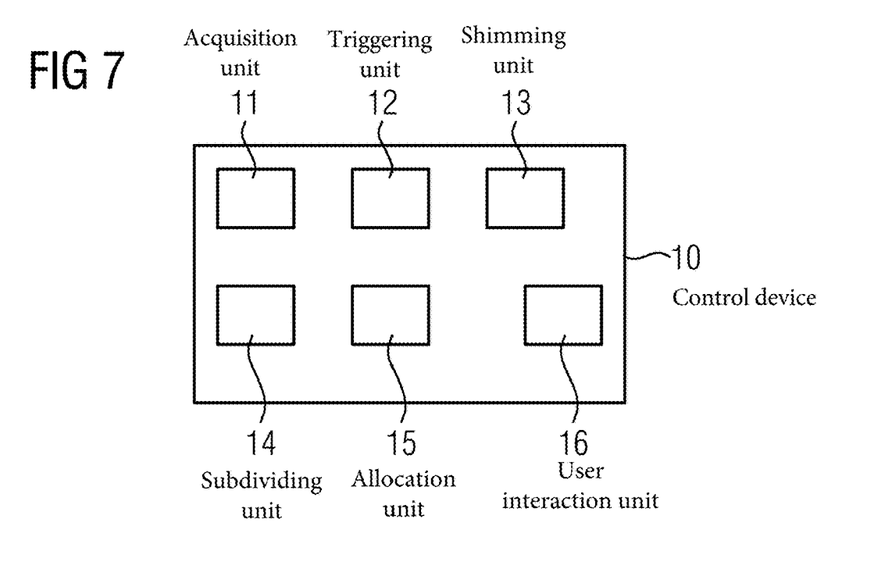
FIG. 7 illustrates an example functional structure of a control device of the magnetic resonance imaging device shown in FIG. 6, in accordance with an embodiment of the present disclosure.

FIG. 7 shows the functional structure of the control device 10. The control device 10 comprises an acquisition unit 11 to control the acquisition of magnetic resonance data, in this example as discussed in step S6 of FIG. 1. The acquisition unit 11 is supported by a triggering unit 12 and a shimming unit 13, wherein the triggering unit 12 evaluates a trigger signal describing the breathing motion of the patient to trigger each concatenation at a certain phase of the breathing cycle. The shimming unit 13 performs the local shimming using a shim device having at least one shim coil, which has not been shown in FIG. 6. The shim boxes as described above may also be used in step S6 as discussed with respect to FIG. 1.

The control device 10 further comprises a subdividing unit 14 for performing the step S4 as discussed with respect to FIG. 1, and an allocation unit 15 for performing the step S5 as discussed with respect to FIG. 1.

In various embodiments, the triggering unit 12 may also be configured to determine breathing characteristics used to choose an adequate first number of concatenations.

Of course, the control device 10 may further comprise a user interaction unit 16 for receiving information entered by the user.

Although the present disclosure has been described in detail with reference to the preferred embodiment, the present disclosure is not limited by the disclosed examples. It is contemplated that a skilled person may derive other variations without departing from the scope of the disclosure.

What is claimed is:

1. A method for acquiring magnetic resonance data of an object with a magnetic resonance imaging apparatus, the method comprising:
   imaging, via the magnetic resonance imaging apparatus, a slice group whose slices define a contiguous imaging volume, the slice group containing a first number of slices;
   acquiring, via the magnetic resonance imaging apparatus, a first number of concatenations of the magnetic resonance data for subgroups of the first number of slices, each one of the subgroups containing a respective second number of slices depending on the first number of concatenations, the subgroups being defined by subdividing the contiguous imaging volume into at least two separate contiguous sub-volumes, with at least two subgroups being defined for each sub-volume, each of the at least two subgroups containing non-adjacent slices in each respective sub-volume;
   performing, via the magnetic resonance imaging apparatus, shimming to increase field homogeneity in the contiguous imaging volume; and
   acquiring, via the magnetic resonance imaging apparatus, the magnetic resonance data of each subgroup by restricting the shimming to at least the sub-volume associated with each respective subgroup,
   wherein the shimming is restricted using a shim box equal to a smallest bounding box of the slices in the respective subgroup.

2. The method according to claim 1, wherein the act of acquiring the magnetic resonance data comprises using at least one frequency-selective preparation pulse as a high-frequency excitation pulse.

3. The method according to claim 1, wherein if the first number of concatenations is even, each sub-volume is defined to be associated with a second number of concatenations equal to an even divisor of the first number of concatenations.

4. The method according to claim 3, wherein two concatenations are associated with each sub-volume such that the number of sub-volumes is half the first number of concatenations.

5. The method according to claim 1, wherein if the first number of concatenations is uneven, an uneven number of sub-volumes is defined to be associated with an uneven second number of concatenations.

6. The method according to claim 5, wherein if the first number of concatenations is larger than five and uneven, (i) a sub-volume that is central with respect to the imaging volume is defined as being associated with three concatenations, and (ii) a plurality of sub-volumes surrounding the central sub-volume are each defined as being associated with two concatenations.

7. The method according to claim 5, wherein if the first number of concatenations is divisible by the uneven second number of concatenations, each of the sub-volumes are defined to be associated with the uneven second number of concatenations.

8. The method according to claim 1, further comprising:
   evaluating at least one admissibility criterion describing first numbers of concatenations to be avoided; and
   upon the admissibility criterion being satisfied, at least one of (i) additional slices, or (ii) additional acquisitions of slices already in a respective slice group, are added as at least one additional concatenation, and the first number of concatenations is correspondingly increased.

9. The method according to claim 8, wherein the at least one admissibility criterion further includes one or more additional criterion that function to determine one or more of (i) whether the first number of concatenations is smaller than a predetermined value, (ii) whether magnetic resonance data from the additional slices is used as a navigator, (iii) whether magnetic resonance data from acquisitions is used as a navigator, and (iv) whether to equalize concatenation distribution in a continuous measurement involving multiple positions of a patient table of the magnetic resonance apparatus.

10. The method according to claim 1, wherein an acquisition of each subgroup is triggered using a trigger signal describing a phase of a periodic motion of a patient to be imaged.

11. The method of claim 10, wherein the first number of concatenations is determined automatically depending on a measurement of the periodic motion of the patient.

12. The method according to claim 1, wherein the act of acquiring the magnetic resonance data includes using at least one of (i) a Turbo Spin Echo (TSE) sequence, and (ii) an Echo-Planar Imaging (EPI) sequence.

13. A magnetic resonance imaging apparatus for acquiring magnetic resonance data of an object, the magnetic resonance imaging apparatus comprising:
a control device; and
a memory storing instructions that, when executed by the control device, cause the magnetic resonance imaging apparatus to:
image a slice group whose slices define a contiguous imaging volume, the slice group containing a first number of slices;
acquire a first number of concatenations of the magnetic resonance data for subgroups of the first number of slices, each one of the subgroups containing a respective second number of slices depending on the first number of concatenations, the subgroups being defined by subdividing the contiguous imaging volume into at least two separate contiguous sub-volumes, with at least two subgroups being defined for each sub-volume, each of the at least two subgroups containing non-adjacent slices in each respective sub-volume;
perform shimming to increase field homogeneity in the contiguous imaging volume; and
acquire the magnetic resonance data of each subgroup by restricting the shimming to at least the sub-volume associated with each respective subgroup,
wherein the shimming is restricted using a shim box equal to a smallest bounding box of the slices in the respective subgroup.

14. A non-transitory computer-readable medium having instructions stored thereon that, when executed by one more processors of a magnetic resonance imaging apparatus, cause the magnetic resonance imaging apparatus to acquire magnetic resonance data of an object by:
imaging a slice group whose slices define a contiguous imaging volume, the slice group containing a first number of slices;
acquiring a first number of concatenations of the magnetic resonance data for subgroups of the first number of slices, each one of the subgroups containing a respective second number of slices depending on the first number of concatenations, the subgroups being defined by subdividing the contiguous imaging volume into at least two separate contiguous sub-volumes, with at least two subgroups being defined for each sub-volume, each of the at least two subgroups containing non-adjacent slices in each respective sub-volume;
performing shimming to increase field homogeneity in the contiguous imaging volume; and
acquiring the magnetic resonance data of each subgroup by restricting the shimming to at least the sub-volume associated with each respective subgroup,
wherein the shimming is restricted using a shim box equal to a smallest bounding box of the slices in the respective subgroup.

* * * * *